United States Patent
Locke et al.

(10) Patent No.: US 9,662,427 B2
(45) Date of Patent: May 30, 2017

(54) INTELLIGENT THERAPY SYSTEM WITH EVAPORATION MANAGEMENT

(71) Applicant: KCI Licensing, Inc., San Antonio, TX (US)

(72) Inventors: Christopher Brian Locke, Bournemouth (GB); Richard Daniel John Coulthard, Verwood (GB); Benjamin A. Pratt, Poole (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 358 days.

(21) Appl. No.: 13/954,658

(22) Filed: Jul. 30, 2013

(65) Prior Publication Data

US 2014/0163490 A1    Jun. 12, 2014

Related U.S. Application Data

(60) Provisional application No. 61/682,449, filed on Aug. 13, 2012.

(51) Int. Cl.
*A41D 13/005*    (2006.01)
*A61M 1/00*    (2006.01)

(52) U.S. Cl.
CPC ........ *A61M 1/0031* (2013.01); *A61M 1/0084* (2013.01); *A61M 1/0088* (2013.01)

(58) Field of Classification Search
CPC ................................................. A61M 1/0031
See application file for complete search history.

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 A1    3/1986
AU    745271       4/1999
(Continued)

OTHER PUBLICATIONS

International Search Report and Written Opinion for corresponding PCT/US2013/052741 mailed May 19, 2014.
(Continued)

*Primary Examiner* — Philip R Wiest
*Assistant Examiner* — Sara Sass

(57) ABSTRACT

Dressings, systems, and methods are disclosed that, in some embodiments, relate to treating a tissue site. In one embodiment, a dressing may include a manifold, a retention pouch, a sealing member, and a conduit interface. The manifold may be adapted to distribute reduced pressure to the tissue site, and the retention pouch may be adapted to retain and manage fluid extracted from the tissue site. The sealing member may cover the retention pouch and the manifold to provide a sealed space with the tissue site. The conduit interface may be in fluid communication with the sealed space and an exterior surface of the sealing member. The dressing may be utilized with a therapy device operable to control reduced pressure in the dressing and fluid flow over the sealing member.

15 Claims, 7 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0004534 A1* | 1/2005 | Lockwood .......... A61M 1/0031 604/304 |
| 2006/0079852 A1* | 4/2006 | Bubb .................. A61F 13/0203 604/317 |
| 2006/0129087 A1* | 6/2006 | Uesugi ................ A61M 13/003 604/26 |
| 2008/0215019 A1 | 9/2008 | Malamutmann |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| GB | 2482337 A | 2/2012 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 2007031765 A1 | 3/2007 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

(56) References Cited

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, ukić, Ž. Maksimović, Đ. . Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

INTELLIGENT THERAPY SYSTEM WITH EVAPORATION MANAGEMENT

RELATED APPLICATION

This application claims the benefit, under 35 USC §119 (e), of the filing of U.S. Provisional Patent Application Ser. No. 61/682,449, entitled "INTELLIGENT THERAPY SYSTEM WITH EVAPORATION MANAGEMENT," filed 13 Aug. 2012, which is incorporated herein by reference for all purposes.

BACKGROUND

The following description relates generally to medical wound care systems, and more particularly, to absorbent dressings, systems, and methods that utilize reduced pressure to treat a tissue site. Depending on the medical circumstances, reduced pressure may be used for, among other things, reduced-pressure therapy to encourage granulation at a tissue site, draining fluids at a tissue site, closing a wound, reducing edema, promoting perfusion, or fluid management.

Common dressings, systems, and methods typically include tubing, external canisters, and other components for providing reduced-pressure therapy. These components may be cumbersome for the patient, expensive, and prone to leaking and blockages. Further, the dressing and associated components may require a particular orientation and installation in order for the patient to receive effective therapy.

Effective management of fluids extracted from a tissue site are important considerations for the patient to receive effective therapy. A leak or blockage in the system can cause a reduction in the effectiveness of the therapy or a complete loss of therapy. Such a situation can occur if too much fluid is present in the dressing.

Thus, improvements that enhance patient comfort and usability while maintaining or exceeding current treatment capabilities are desirable. Further, improvements in system monitoring capabilities during therapy can increase reliability by providing accurate information to a user regarding any unfavorable conditions that may require corrective action.

SUMMARY

Shortcomings with certain aspects of tissue treatment methods, dressings, and systems are addressed as shown and described in a variety of illustrative, non-limiting embodiments herein.

According to a first illustrative, non-limiting embodiment, a system for treating a tissue site on a patient includes a dressing and a therapy device. The dressing includes a manifold, a retention pouch, a sealing member, and conduit interface. The manifold is adapted to be positioned adjacent the tissue site and is comprised of a hydrophobic material that is fluid permeable. The retention pouch is adapted to be positioned adjacent the manifold and adapted to retain fluid. The retention pouch includes an expandable portion and a recess. The expandable portion is adapted to expand to retain fluid in the retention pouch, and the recess is adapted to substantially preclude expansion. The sealing member has an exterior surface and is adapted to cover the retention pouch and the manifold to provide a sealed space between the tissue site and the sealing member. At least a portion of the sealing member is comprised of a material that allows vapor to egress from the sealed space through the sealing member. The conduit interface is coupled to the sealing member.

The conduit interface of the first embodiment includes an evaporative flow conduit, a variable pressure conduit, a reduced-pressure conduit, and a manifold pressure conduit. The evaporative flow conduit is in fluid communication with the exterior surface of the sealing member. The variable pressure conduit has an inlet in fluid communication with the sealed space. The inlet of the variable pressure conduit is positioned to be in a spaced relationship relative to the expandable portion of the retention pouch. The reduced-pressure conduit has an inlet in fluid communication with the sealed space. The inlet of the reduced-pressure conduit is positioned to be in a spaced relationship relative to the recess in the retention pouch. The manifold pressure conduit has an inlet in fluid communication with the manifold. The inlet of the manifold pressure conduit is positioned between the retention pouch and the manifold.

The therapy device of the first embodiment includes a fluid flow source, a variable pressure sensor, a reduced-pressure source, a manifold pressure sensor, and a controller. The fluid flow source is in fluid communication with the evaporative flow conduit. The variable pressure sensor is in fluid communication with the variable pressure conduit. The reduced-pressure source is in fluid communication with the reduced-pressure conduit. The manifold pressure sensor is in fluid communication with the manifold pressure conduit. The controller is adapted to receive a variable pressure signal from the variable pressure sensor and a manifold pressure signal from the manifold pressure sensor. The controller is operable to provide a reduced pressure output from the reduced-pressure source when the manifold pressure signal is greater than a target reduced pressure. Further, the controller is operable to increase a fluid flow rate from the fluid flow source in response to an increase in a pressure differential between the variable pressure signal and the manifold pressure signal.

According to a second illustrative, non-limiting embodiment, a system for treating a tissue site on a patient includes a dressing and a therapy device. The dressing includes a manifold, a retention pouch, a sealing member, and a conduit interface. The manifold has a first side and a second side, the first side facing opposite the second side. The first side of the manifold is adapted to be positioned adjacent the tissue site. The retention pouch is adapted to retain a fluid and to be positioned adjacent the second side of the manifold. The retention pouch includes an absorbent core encapsulated between a first permeable layer and a second permeable layer. Additionally, the retention pouch includes an expandable portion and a recess. The sealing member has an exterior surface and is adapted to cover the retention pouch and the manifold to provide a sealed space between the sealing member and the tissue site. The conduit interface is coupled to the sealing member.

The conduit interface in the second embodiment includes an evaporative flow conduit, a variable pressure conduit, a reduced-pressure conduit, and a manifold pressure conduit. The evaporative flow conduit is in fluid communication with the exterior surface of the sealing member. The variable pressure conduit has an inlet in fluid communication with the sealed space. The inlet of the variable pressure conduit is substantially aligned with and separated from the expandable portion of the retention pouch. The reduced-pressure conduit has an inlet in fluid communication with the sealed space. The inlet of the reduced-pressure conduit is substantially aligned with and separated from the recess in the retention pouch. The manifold pressure conduit has an inlet in fluid communication with the manifold. The inlet of the manifold pressure conduit is positioned between the retention pouch and the second side of the manifold.

The therapy device of the second embodiment includes a fluid flow source, a variable pressure sensor, a reduced-pressure source, a manifold pressure sensor, and a controller. The fluid flow source is in fluid communication with the evaporative flow conduit. The variable pressure sensor is in fluid communication with the variable pressure conduit. The reduced-pressure source is in fluid communication with the reduced-pressure conduit. The manifold pressure sensor is in fluid communication with the manifold pressure conduit. The controller is adapted to receive a variable pressure signal from the variable pressure sensor and a manifold pressure signal from the manifold pressure sensor. The controller is operable to provide a reduced pressure output from the reduced-pressure source when the manifold pressure signal is greater than a target reduced pressure. Further, the controller is operable to increase a fluid flow rate from the fluid flow source in response to an increase in a pressure differential between the variable pressure signal and the manifold pressure signal.

According to a third illustrative, non-limiting embodiment, a dressing for treating a tissue site on a patient includes a manifold, a retention pouch, a sealing member, and a conduit interface. The manifold includes a fluid permeable, hydrophobic material. The manifold has a first side and a second side. The first side of the manifold is adapted to be positioned adjacent the tissue site. The retention pouch is adapted to be positioned adjacent the second side of the manifold and to retain a fluid. The retention pouch includes an expandable portion and a recess. The expandable portion is adapted to expand to retain the fluid, and the recess is adapted to substantially preclude expansion. The sealing member has an exterior surface and is adapted to cover the retention pouch and the manifold to provide a sealed space between the tissue site and the sealing member. At least a portion of the sealing member is comprised of a vapor-permeable material that allows vapor to egress from the sealed space through the sealing member. The conduit interface is coupled to the sealing member.

The conduit interface of the third embodiment includes an evaporative flow conduit, a variable pressure conduit, a reduced-pressure conduit, and a manifold pressure conduit. The evaporative flow conduit is in fluid communication with the exterior surface of the sealing member. The variable pressure conduit has an inlet in fluid communication with the sealed space. The inlet of the variable pressure conduit is positioned to be in a spaced relationship relative to the expandable portion of the retention pouch. The reduced-pressure conduit has an inlet in fluid communication with the sealed space. The inlet of the reduced-pressure conduit is positioned to be in a spaced relationship relative to the recess in the retention pouch. The manifold pressure conduit has an inlet in fluid communication with the manifold. The inlet of the manifold pressure conduit is positioned between the retention pouch and the manifold.

According to a fourth illustrative, non-limiting embodiment, a method of treating a tissue site on a patient includes the steps of positioning a manifold over the tissue site, and positioning a retention pouch adapted to retain a fluid over the manifold. The retention pouch includes an expandable portion and a recess. When the retention pouch retains a fluid, the expandable portion is adapted to increase in size and the recess is adapted to remain a substantially constant size. The method additionally includes the step of covering the retention pouch and the manifold with a sealing member to provide a sealed space between the tissue site and the sealing member. The sealing member has an exterior surface, and at least a portion of the sealing member is comprised of a vapor-permeable material that allows vapor to egress from the sealed space. Further, the method includes the steps of providing a reduced-pressure conduit in fluid communication with the sealed space, and providing a variable pressure conduit in fluid communication with the sealed space. The reduced-pressure conduit has an inlet positioned in a spaced relationship relative to the recess in the retention pouch. The variable pressure conduit has an inlet positioned in a spaced relationship relative to the expandable portion of the retention pouch. Further, the method includes the step of measuring a manifold pressure between the manifold and the retention pouch. The manifold pressure corresponds to a reduced pressure at the tissue site. Further, the method includes the step of applying reduced pressure to the sealed space through the reduced-pressure conduit until the manifold pressure reaches a target reduced pressure. The application of reduced pressure to the sealed space extracts fluid from the tissue site. The expandable portion of the retention pouch expands to retain the extracted fluid. Further, the method includes the step of measuring a variable pressure between the expandable portion of the retention pouch and the sealing member at the inlet of the variable pressure conduit. Further, the method includes the steps of calculating a differential pressure between the manifold pressure and the variable pressure, and providing a fluid flow over the exterior surface of the sealing member. The differential pressure corresponds to the amount of fluid retained by the retention pouch. The fluid flow has a flow rate substantially corresponding to the differential pressure. The fluid flow over the sealing member evaporates the fluid extracted from the tissue site.

Other features and advantages of the illustrative embodiments will become apparent with reference to the drawings and detailed description that follow.

BRIEF DESCRIPTION OF THE DRAWINGS

A more complete understanding of this specification may be obtained by reference to the following detailed description when taken in conjunction with the accompanying drawings wherein.

DETAILED DESCRIPTION

In the following detailed description of non-limiting, illustrative embodiments, reference is made to the accompanying drawings that form a part hereof. Other embodiments may be utilized, and logical, structural, mechanical, electrical, and chemical changes may be made without departing from the scope of this specification. To avoid detail not necessary to enable those skilled in the art to practice the embodiments described herein, the description may omit certain information known to those skilled in the art. Thus, the following detailed description is provided without limitation and with the scope of the illustrative embodiments being defined by the appended claims.

Figure 1:
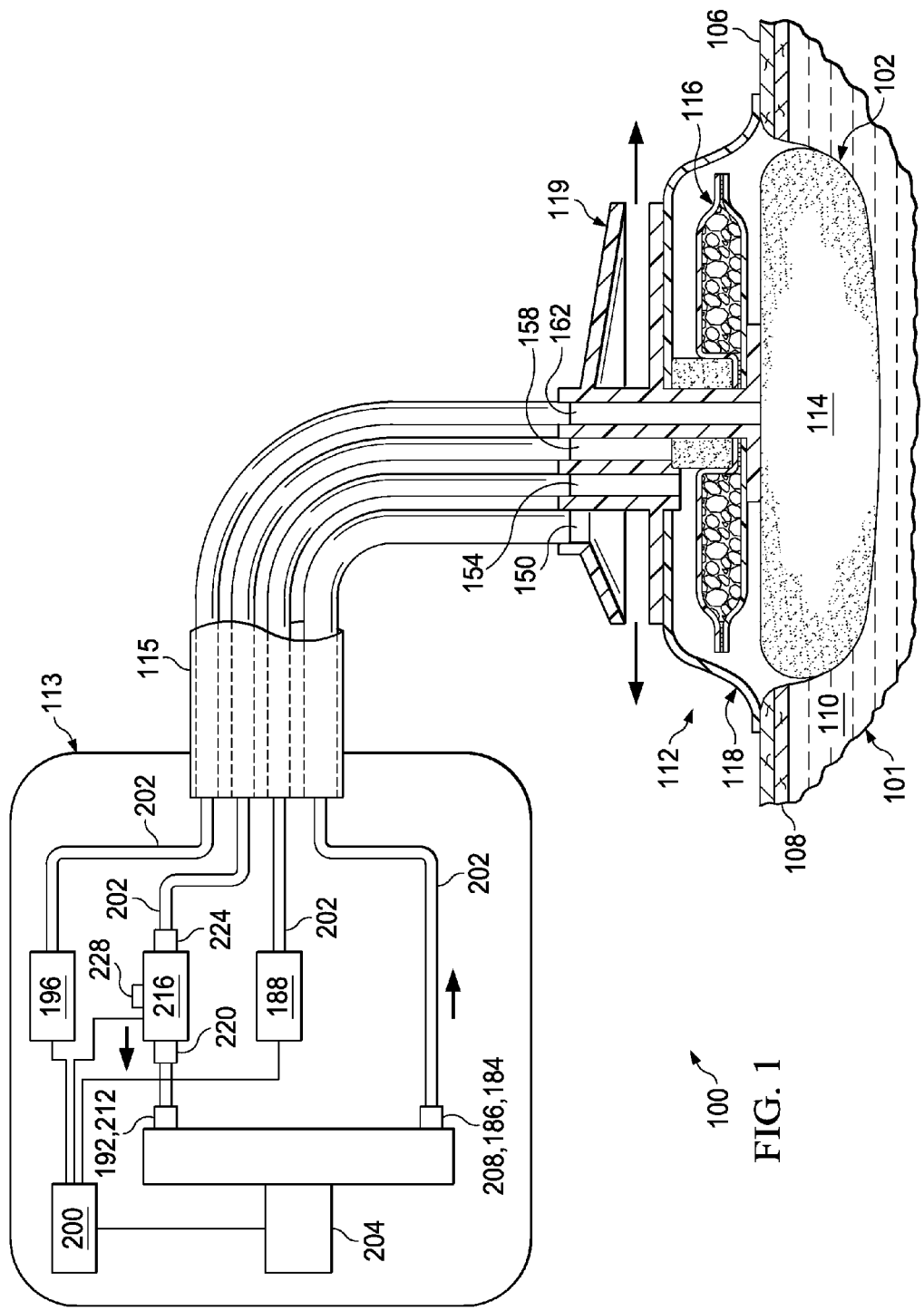
FIG. 1 is a schematic of an illustrative embodiment of a system for treating a tissue site on a patient.
Figure 2:
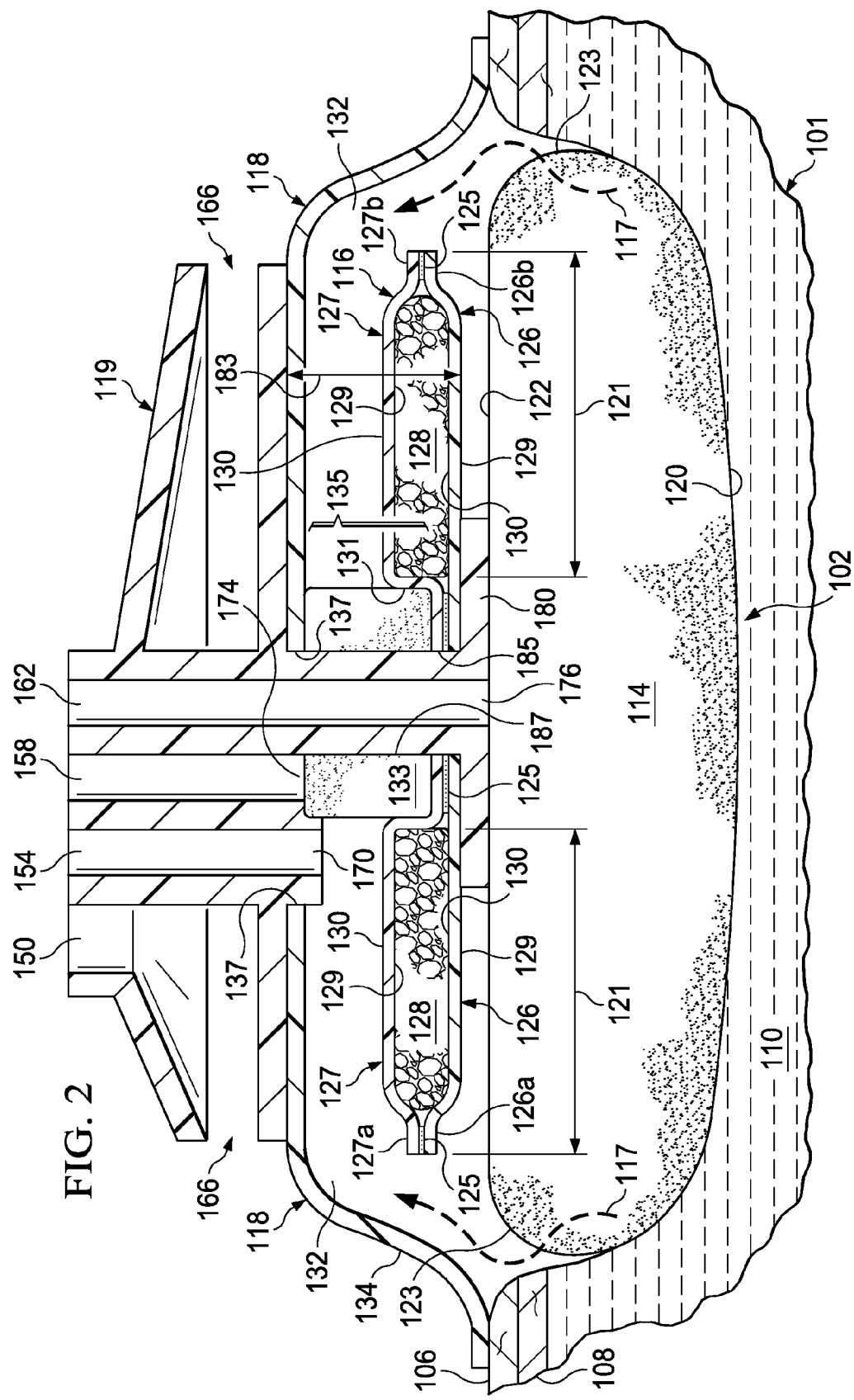
FIG. 2 is a cut-away view of an illustrative embodiment of a dressing depicted in FIG. 1.
Figure 3:
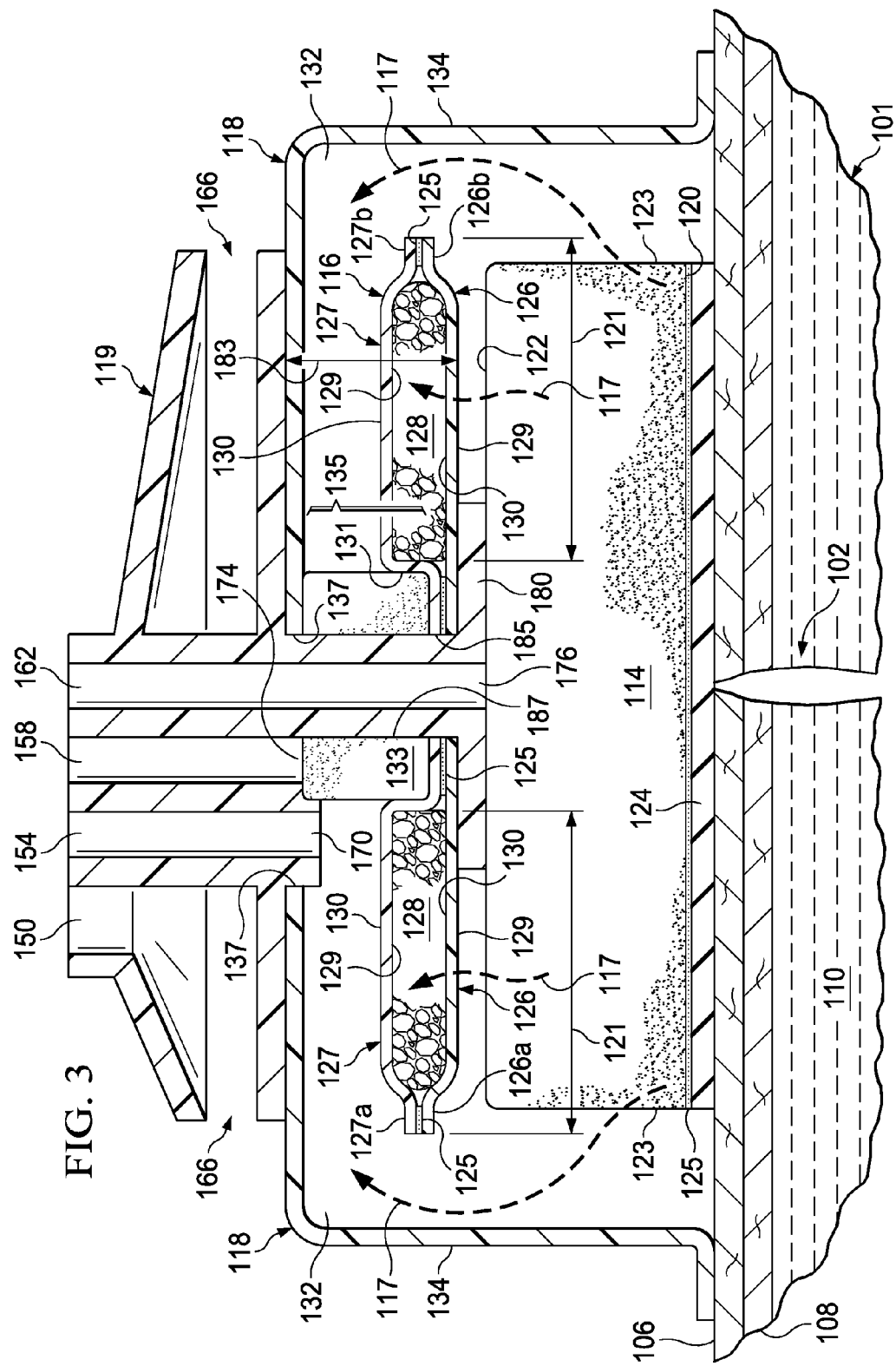
FIG. 3 is a cut-away view of an another illustrative embodiment of a dressing.
Figure 4:
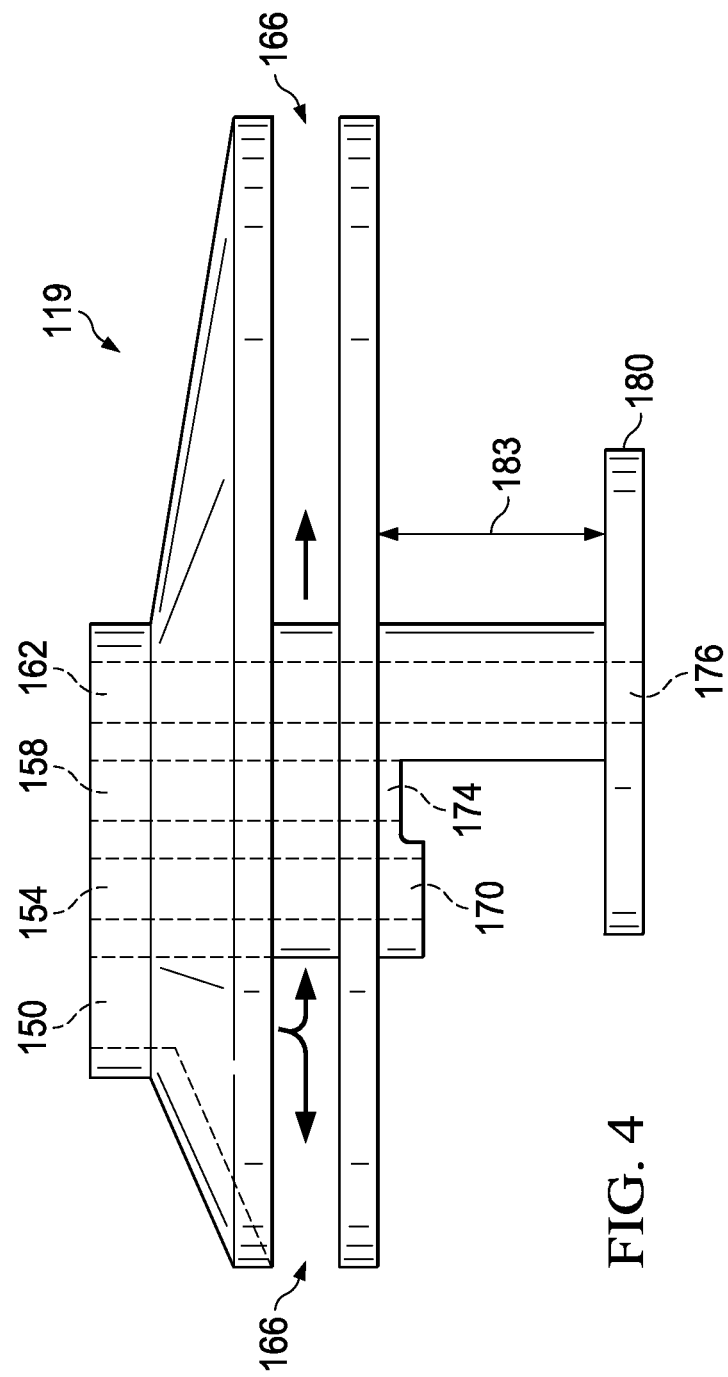
FIG. 4 is a side view of an illustrative embodiment of a conduit interface depicted in FIGS. 1-3.
Figure 5:
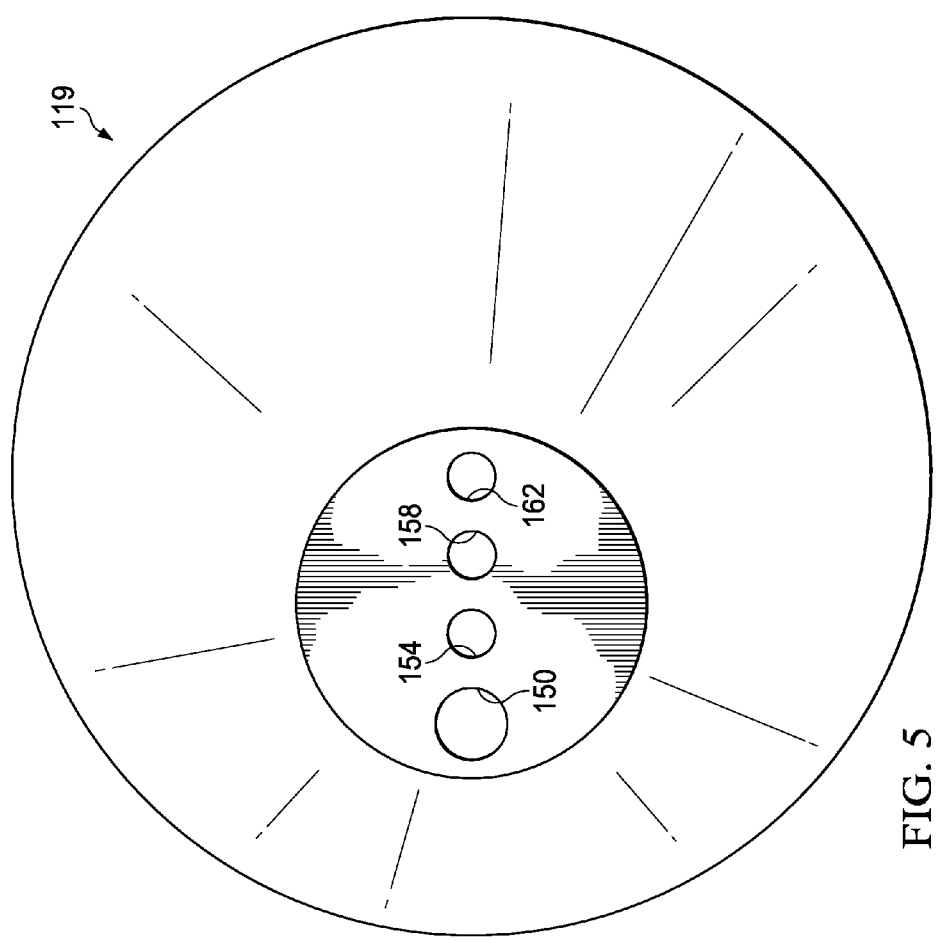
FIG. 5 is a top view of the conduit interface depicted in FIG. 4.

Referring to the drawings, FIG. 1 depicts an illustrative embodiment of a treatment system 100 for treating a tissue site 102 on a patient 101. The tissue site 102 may be, for example, a wound, such as an open wound shown in FIG. 2, or an incision as shown in FIG. 3. The tissue site 102 may extend through or otherwise involve an epidermis 106, a dermis 108, and a subcutaneous tissue 110. The treatment system 100 may also be used at other tissue sites without limitation. Further, the tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. The treatment of tissue site 102 may include removal of fluids, such as exudate or ascites.

The treatment system 100 may include a dressing 112 and a therapy device 113. A fluid communication conduit 115 may provide fluid communication between the dressing 112 and the therapy device 113. The therapy device 113 may apply internal reduced pressure and an external fluid flow to the dressing 112 through the fluid communication conduit 115 for treating the tissue site 102 as will be described further below. Further, the therapy device 113 may control the application of reduced pressure and fluid flow according to pressure feedback signals received from the dressing 112 through the fluid communication conduit 115.

Referring now to FIGS. 1-5, in one embodiment, the dressing 112 may include a manifold 114, a retention pouch 116, a sealing member 118, and a conduit interface 119. The manifold 114 may have a first side 120, a second side 122, and edges 123. The first side 120 and the second side 122 may terminate at edges 123 and face in opposite directions from one another. The first side 120 of the manifold 114 may be adapted to face inward toward the tissue site 102. The manifold 114 may include a plurality of flexibility notches or recesses (not shown) that may be lateral cuts in the manifold 114. The manifold 114 may include one or more longitudinal cuts or other cuts. The flexibility notches may enhance the flexibility of the manifold 114. The enhanced flexibility may be particularly useful when the dressing 112 is applied over a joint or other area of movement. The manifold 114 may also be referred to as a dressing bolster.

The manifold 114 may be formed from any manifold material or flexible bolster material that provides a vacuum space, or treatment space, such as, for example, a porous and permeable foam or foam-like material, a member formed with pathways, a graft, a gauze, or other similar material. As a more specific, non-limiting example, the manifold 114 may be a reticulated, open-cell polyurethane or polyether foam that provides good permeability of fluids while under a reduced pressure. One such foam material is VAC® GranuFoam® material available from Kinetic Concepts, Inc. (KCI) of San Antonio, Tex. Any material or combination of materials may be used as a manifold material for the manifold 114 provided that the manifold material is operable to distribute reduced pressure. The term "manifold" as used herein generally refers to a substance or structure that is provided to assist in applying reduced pressure to, delivering fluids to, or removing fluids from a tissue site. A manifold may include a plurality of flow channels or pathways. The plurality of flow channels may be interconnected to improve distribution of fluids provided to and removed from the area of tissue around the manifold. Further examples of manifolds may include, without limitation, devices that have structural elements arranged to form flow channels, cellular foam, such as open-cell foam, porous tissue collections, and liquids, gels, and foams that include or cure to include flow channels.

A material with a higher or lower density, or different pore size, than GranuFoam® material may be desirable for the manifold 114 depending on the application. Among the many possible materials, for example, the following may be used: GranuFoam® material; Foamex® technical foam (www.foamex.com); molded bed of nails structures; patterned grid material, such as those manufactured by Sercol Industrial Fabrics; 3D textiles, such as those manufactured by Baltex of Derby, U.K.; a gauze; a flexible channel-containing member; or a graft. In some instances it may be desirable to add ionic silver to the foam in a micro bonding process, or to add other substances to the material, such as antimicrobial agents.

In one embodiment, the manifold 114 may be a hydrophobic layer. The hydrophobic characteristics of the manifold 114 may prevent the manifold 114 from directly absorbing fluid, such as exudate, from the tissue site 102, but allow the fluid to pass through. Thus, as depicted by the fluid communication arrows 117 in FIGS. 2 and 3, the fluid may be drawn away from the tissue site 102 as will be described below. Further, upon application of reduced pressure, the porous foam-like nature of the manifold 114 as described above may permit the manifold 114 to contract and apply a compressive force capable of closing a wound, such as the incision illustrated in FIG. 3.

Referring to FIG. 3, in one embodiment, a comfort layer 124 may be coupled, for example, by a heat bond 125 or any other suitable technique, to the first side 120 of the manifold 114. The comfort layer 124 may provide comfort to the patient 101 when the manifold 114 is placed adjacent to the epidermis 106 of the patient 101. The comfort layer 124 may be any material that helps prevent skin irritation and discomfort while allowing fluid transmission through the comfort layer 124. As a non-limiting example, a woven elastic material or a polyester knit textile substrate may be used. As another non-limiting example, an InterDry™ textile material from Milliken Chemical of Spartanburg, S.C., may be used. The comfort layer 124 may include anti-microbial substances, such as silver.

As used herein, the term "coupled" includes coupling via a separate object and direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid may be in communication between the designated parts or locations.

Continuing with FIGS. 1-5, the retention pouch 116 may include a first permeable layer 126, a second permeable layer 127, and an absorbent core 128. In one embodiment, the absorbent core 128 may be encapsulated between the first permeable layer 126 and the second permeable layer 127. The first permeable layer 126 may have edges 126a,b secured respectively to edges 127a,b of the second permeable layer 127 around or otherwise encapsulating the absorbent core 128. The edges 126a,b and 127a,b of the first and the second permeable layers 126, 127 may be secured to one another in any suitable manner, such as, for example by the heat bond 125 described above.

The retention pouch 116 may be adapted to retain fluid, such as fluid extracted from the tissue site 102. The first permeable layer 126 and the second permeable layer 127 may each have a fluid acquisition surface 129 facing in an opposite direction from a wicking surface 130. The wicking surfaces 130 of the first and second permeable layers 126, 127 may each have a grain (not shown) oriented in a longitudinal direction along the length of the dressing 112. The orientation of the grain of the wicking surfaces 130 may serve to wick fluid, such as fluid extracted from the tissue site 102, along the length of the dressing 112. The wicking of fluid in this manner may enhance the ability of the retention pouch 116 to retain and manage fluid efficiently for preventing clogs as will be described in further detail below.

The retention pouch 116 may additionally include a recess 131 and an expandable portion 121. When the retention pouch 116 retains a fluid as described above, the expandable portion 121 may be adapted to increase in size, and the recess 131 may be adapted to remain a substantially constant size. For example, in one embodiment, the first and the second permeable layers 126, 127 may be coupled to one another in any suitable manner, such as with the heat bond 125 described above, to provide the recess 131. Thus, the coupling of the first and the second permeable layers 126, 127 to one another may substantially preclude expansion of the recess 131. However, the expandable portion 121 of the retention pouch 116 may be free of restriction and capable of expanding to accommodate fluid being retained in the retention pouch 116 and the absorbent core 128. Further, in another embodiment, the expandable portion 121 may extend radially outward from the recess 131. Additionally, in yet another illustrative embodiment, the recess 131 may be capable of receiving or otherwise accommodating a filter 133. For example, the filter 133 may be positioned in a gap 135 that may be defined between the recess 131 and the sealing member 118, described below. The recess 131 and the filter 133 may further enhance the ability of the dressing 112 to resist clogging.

The first and the second permeable layers 126, 127 may be any material exhibiting the fluid acquisition and wicking characteristics described above, such as, for example, Libeltex TDL2, manufactured by Libeltex. Further, the filter 133 may comprise, for example, any hydrophobic material, and the filter 133 may have any suitable shape, such as a 3-dimensional shape.

The absorbent core 128 may be any absorbent material for retaining liquids and may, for example, include one or more of the following: Luquafleece® material; BASF 402c; Technical Absorbents 2317 available from Technical Absorbents (www.techabsorbents.com); sodium polyacrylate super absorbers; cellulosics (carboxy methyl cellulose and salts such as sodium CMC); or alginates. The absorbent core 128 may allow fluids and exudate removed from the tissue site 102 to be stored within the retention pouch 116 rather than external to the dressing 112.

Similar to the manifold 114, the absorbent core 128 of the retention pouch 116 may include a plurality of flexibility notches (not shown) or recesses that may be lateral cuts in the absorbent core 128. The absorbent core 128 may include one or more longitudinal cuts or other cuts. The flexibility notches may enhance the flexibility of the retention pouch 116, and may thereby increase the ability of the retention pouch 116 to conform to, for example, the joint of a patient. Further, the enhanced flexibility may assist in preventing any interference with the ability of the manifold 114 to contract as described above.

The retention pouch 116 may have a maximum fluid capacity. At the maximum fluid capacity of the retention pouch 116, fluid communication through the retention pouch 116 may be substantially precluded. The retention pouch 116 may have a maximum fluid capacity of any amount to suit a particular application.

In one embodiment, the manifold 114 may be positioned between the tissue site 102 and the retention pouch 116 with the first side 120 of the manifold 114 facing the tissue site 102. In this embodiment, the fluid acquisition surface 129 of the first permeable layer 126 may be positioned proximate to and facing the second side 122 of the manifold 114, and the fluid acquisition surface 129 of the second permeable layer 127 may be positioned facing the absorbent core 128.

The sealing member 118 may provide a cover over the manifold 114, the retention pouch 116, and at least a portion of the epidermis 106 of the patient 101. The sealing member 118 may be positioned over the manifold 114 and the retention pouch 116, and may provide a sealed space 132 between the sealing member 118 and the tissue site 102. The sealing member 118 may have an exterior surface 134 exposed to ambient air. Further, a portion of the sealing member 118 may include a sealing member aperture 137 to allow fluid communication between the therapy device 113 and the sealed space 132, the retention pouch 116, the manifold 114, and the tissue site 102.

In one embodiment, the second permeable layer 127 of the retention pouch 116 may face the sealing member 118. In this embodiment, the recess 131 may be positioned on the second permeable layer 127 and facing the sealing member 118.

The sealing member 118 may be formed from any material that allows for a fluid seal. "Fluid seal," or "seal," means a seal adequate to maintain reduced pressure at a desired site given the particular reduced pressure source or system involved. The sealing member 118 may be sealed, for example, against the epidermis 106 or against a gasket or drape by a sealing apparatus, such as a pressure-sensitive adhesive. Further, the sealing apparatus may be, for example, an adhesive sealing tape, drape tape or strip, double-side drape tape, pressure-sensitive adhesive, paste, hydrocolloid, hydrogel, or other similar material. If a tape is used, the tape may be formed of the same material as the sealing member 118 with a pre-applied, pressure-sensitive adhesive. The pressure-sensitive adhesive may be applied on a patient-facing side of the sealing-member 118 or portion thereof. Before the sealing member 118 is secured to the epidermis 106, removable strips covering the pressure-sensitive adhesive may be removed.

In one embodiment, at least a portion of the sealing member 118 comprises a liquid-impervious material that allows moisture vapor to egress from the sealed space 132 through the sealing member 118 and to the atmosphere. For example, the sealing member 118 may be formed from a high-moisture-vapor-transfer-rate material (high MVTR material) or a drape material that may be a flexible film. "Moisture Vapor Transmission Rate" or "MVTR" may represent the amount of moisture that can pass through a material in a given period of time. A high-moisture-vapor-transfer-rate material may have a moisture vapor transmission rate greater than about 300 $g/m^2$ per a 24 hour period, or more specifically, greater than about 1000 $g/m^2$ per a 24 hour period.

The sealing member 118 may comprise, for example, one or more of the following materials: hydrophilic polyurethane; cellulosics; hydrophilic polyamides; an INSPIRE 2301 material from Expopack Advanced Coatings of Wrexham, United Kingdom; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example from Arkema, France; or other appropriate material. The sealing member 118 may be a hybrid drape formed of a combination of the previously described materials and may have a lower silicone layer (not shown) having perforated regions of exposed acrylic adhesive for securing the sealing member 118 to the patient 101 as previously described.

The conduit interface 119 may be coupled to the sealing member 118 of the dressing 112. The conduit interface 119 may be in fluid communication with the exterior surface 134 of the sealing member 118. Further, the conduit interface 119 may be in fluid communication with the sealed space 132 through the sealing member aperture 137 in the sealing member 118. The fluid communication conduit 115 may provide fluid communication between the therapy device 113 and the conduit interface 119.

The conduit interface 119 may include an evaporative flow conduit 150, a variable pressure conduit 154, a reduced-pressure conduit 158, and a manifold pressure conduit 162. The evaporative flow conduit 150 may be in fluid communication with the exterior surface 134 of the sealing member 118. The conduit interface 119 may include an evaporative flow outlet 166 in fluid communication with the evaporative flow conduit 150. In one embodiment, the evaporative flow outlet 166 may be positioned circumferentially about the conduit interface 119 for providing circumferential fluid flow about the conduit interface 119 and over the exterior surface 134 of the sealing member 118.

The conduit interface 119 may be formed from a medical-grade, soft polymer or other pliable material. As non-limiting examples, the conduit interface 119 may be formed from polyurethane, polyethylene, polyvinyl chloride (PVC), fluorosilicone, ethylene-propylene, or other similar materials. In one illustrative, non-limiting embodiment, conduit interface 119 may be molded from DEHP-free PVC. The conduit interface 119 may be formed in any suitable manner such as by molding, casting, machining, or extruding. Further, the conduit interface 119 may be formed as an integral unit or as individual components.

The variable pressure conduit 154 may have an inlet 170 in fluid communication with the sealed space 132. The inlet 170 of the variable pressure conduit 154 may be positioned in a spaced relationship relative to the expandable portion 121 of the retention pouch 116. In one embodiment, the inlet 170 of the variable pressure conduit 154 may be substantially aligned over the expandable portion 121 and the second permeable layer 127 of the retention pouch 116. Further, the inlet 170 of the variable pressure conduit 154 may be positioned between the retention pouch 116 and the sealing member 118.

The reduced-pressure conduit 158 may have an inlet 174 in fluid communication with the sealed space 132. The inlet 174 of the reduced-pressure conduit 158 may be positioned in a spaced relationship relative to the recess 131 in the retention pouch 116. The recess 131 may provide the gap 135. The gap 135 may be between the inlet 174 of the reduced-pressure conduit 158 and the retention pouch 116. In one embodiment, the inlet 174 of the reduced-pressure conduit 158 may be substantially aligned over the recess 131 and the second permeable layer 127 of the retention pouch 116. Further, the inlet 174 of the reduced-pressure conduit 158 may be positioned between the retention pouch 116 and the sealing member 118.

The manifold pressure conduit 162 may have an inlet 176 in fluid communication with the manifold 114. The inlet 176 of the manifold pressure conduit 162 may be positioned between the retention pouch 116 and the manifold 114. In one embodiment, the inlet 176 of the manifold pressure conduit 162 may be positioned adjacent to the second side 122 of the manifold 114. The manifold pressure conduit 162 may also be in fluid communication with the tissue site 102, the sealed space 132, and the components of the dressing 112 by virtue of the fluid permeability of the manifold 114.

In one embodiment, the conduit interface 119 may include a base 180 coupled at the inlet 176 of the manifold pressure conduit 162. In this embodiment, the manifold pressure conduit 162 may have a length 183 between the base 180 and the exterior surface 134 of the sealing member 118. For example, the length 183 may be a length that the manifold pressure conduit 162 extends into the sealed space 132 of the dressing 112 from the exterior surface 134 of the sealing member 118. The manifold pressure conduit 162 may extend through a retention pouch aperture 185 disposed, for example, through the recess 131 in the retention pouch 116. Similarly, the manifold pressure conduit 162 may extend through a filter aperture 187 disposed through the filter 133. The base 180 may extend laterally outward from the inlet 176 of the manifold pressure conduit 162 and underneath the retention pouch 116. The base 180 may carry the retention pouch 116 between the base 180 and the sealing member 118 such that the expandable portion 121 of the retention pouch 116 extends laterally beyond the base 180. The length 183 of the manifold pressure conduit 162 may be sized according to the thickness of the retention pouch 116. For example, the length 183 may provide space for the expandable portion 121 of the retention pouch 116 to increase in size prior to contacting the inlet 170 of the variable pressure conduit 154, as described below. In one embodiment, the length 183 may be about 2.5 times the thickness of the retention pouch 116.

In another embodiment, the conduit interface 119 may include a membrane filter (not shown) in fluid communication with the sealing member aperture 137 for prevention of clogs and transmission of odors from the dressing 112 during therapy. The membrane filter may be, for example, a hydrophobic or oleophobic filter. Additionally, the membrane filter may include a substance, such as, for example, charcoal for controlling odor. The membrane filter may be replaceable or formed integrally with the conduit interface 119. In another embodiment, the membrane filter may be positioned in any suitable location in fluid communication between the dressing 112 and the therapy device 113.

The therapy device 113 may include a fluid flow source 184, a variable pressure sensor 188, a reduced-pressure source 192, a manifold pressure sensor 196, and a controller 200. The fluid flow source 184 may be in fluid communication with the evaporative flow conduit 150. The variable pressure sensor 188 may be in fluid communication with the variable pressure conduit 154. The reduced-pressure source 192 may be in fluid communication with the reduced-pressure conduit 158. The manifold pressure sensor 196 may be in fluid communication with the manifold pressure conduit 162. In one embodiment, the fluid communication conduit 115 may include a plurality of fluid communication lumens 202 that provide fluid communication between each of the previously described components of the therapy device 113 and the conduit interface 119. In another embodiment, the fluid communication lumens 202 may be provided as individual components rather than as a part of the fluid communication conduit 115.

The fluid flow source 184 may provide fluid flow as a part of the therapy device 113 in the treatment system 100. In one embodiment, the fluid flow source 184 may be a positive-pressure source 186 that provides a positive-pressure output to the evaporative flow conduit 150 for supplying fluid flow from the therapy device 113 to the exterior surface 134 of the sealing member 118. The fluid flow may have a variable flow rate as will be discussed below. The fluid flow source 184 may be any suitable device or source for providing fluid flow, such as, for example, a pump or blower.

In another embodiment, the fluid flow source 184 may be any source of fluid flow over the exterior surface 134 of the sealing member 118. For example, the fluid flow source 184 may be ambient air directed over the exterior surface 134 of the sealing member 118. Further, the fluid flow source 184 may be reduced pressure applied to the evaporative flow conduit 150 for drawing fluid across the exterior surface 134 of the sealing member 118 and back to the therapy device 113.

As a part of the therapy device 113 in the treatment system 100, the reduced-pressure source 192 may provide reduced pressure to the dressing 112. In one embodiment, the reduced-pressure source 192 may provide a reduced pressure output to the reduced-pressure conduit 158 for applying reduced pressure to the sealed space 132, the retention pouch 116, the manifold 114, and the tissue site 102. The reduced-pressure source 192 may be any suitable device for providing reduced pressure as described herein, such as, for example, a vacuum pump, wall suction, or other source.

As used herein, "reduced pressure" generally refers to a pressure less than the ambient pressure at the tissue site 102 being subjected to treatment. In one embodiment, the reduced pressure may be less than the atmospheric pressure. In another embodiment, the reduced pressure may be less than a hydrostatic pressure at a tissue site. Unless otherwise indicated, values of pressure stated herein are gauge pressures. While the amount and nature of reduced pressure applied to a tissue site may vary according to the application, the reduced pressure may be between about −5 mm Hg to about −500 mm Hg, and more specifically, between about −100 mm Hg to about −200 mm Hg.

The reduced pressure delivered may be constant or varied (patterned or random) and may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, an increase in reduced pressure or vacuum pressure may refer to a relative reduction in absolute pressure. An increase in reduced pressure corresponds to a reduction in pressure (more negative relative to ambient pressure) and a decrease in reduced pressure corresponds to an increase in pressure (less negative relative to ambient pressure).

The controller 200 may be a printed wire assembly (PWA) or an application specific integrated circuit (ASIC) or other control device. The controller 200 may be adapted to receive a variable pressure signal from the variable pressure sensor 188 and a manifold pressure signal from the manifold pressure sensor 196. Reduced pressure communicated from the variable pressure conduit 154 to the variable pressure sensor 188 may provide the variable pressure signal, and reduced pressure communicated from the manifold pressure conduit 162 to the manifold pressure sensor 196 may provide the manifold pressure signal. The controller 200 may receive the variable pressure signal and the manifold pressure signal in any suitable manner, such as, for example, by wired or wireless electronic communication.

The controller 200 may be operable to provide the reduced pressure output from the reduced-pressure source 192 when the manifold pressure signal is greater than a target reduced pressure. For example, the reduced pressure output may be provided when the reduced pressure corresponding to the manifold pressure signal is less negative relative to ambient pressure than the target reduced pressure. Conversely, the controller 200 may cease or preclude the reduced pressure output from the reduced-pressure source 192 when the manifold pressure signal has reached the target reduced pressure. Further, the controller 200 may control the reduced pressure output from the reduced-pressure source 192 to the dressing 112 when the manifold pressure signal falls within a threshold of the target reduced pressure. In this manner, the controller 200 may be capable of maintaining the reduced pressure in the dressing 112 at the target reduced pressure or within a threshold thereof. The target reduced pressure may be any reduced pressure to suit a particular application for the dressing 112. For example, the target reduced pressure may be input by a user into a control panel (not shown) or other input device associated with the controller 200.

Further, the controller 200 may be operable to increase the flow rate from the fluid flow source 184 in response to an increase in a pressure differential between the variable pressure signal and the manifold pressure signal. The controller 200 may also be operable to decrease the flow rate from the fluid flow source 184 in response to a decrease in the pressure differential between the variable pressure signal and the manifold pressure signal. The pressure differential between the variable pressure signal and the manifold pressure signal is the difference between the variable pressure signal and the manifold pressure signal. As will be described in further detail below, an increase in the pressure differential may correspond to a pressure drop across the retention pouch 116. The pressure differential and the pressure drop may correspond to an increase in the amount of moisture in the dressing 112. Thus, the controller 200 may control the rate of evaporation of moisture retained in the dressing 112 by varying the flow rate of fluid across the sealing member 118 according to the level of moisture in the dressing 112.

For example, in the embodiment depicted in FIG. 1, a pump 204 may provide both the fluid flow source 184 and the reduced-pressure source 192. The pump 204 may have a pump outlet 208 and a pump inlet 212. In this embodiment, the pump outlet 208 may provide the positive-pressure source 186 as the fluid flow source 184, and the pump inlet 212 may provide the reduced-pressure source 192. The pump outlet 208 may be in fluid communication with the evaporative flow conduit 150, and the pump inlet 212 may be in fluid communication with the reduced-pressure conduit 158.

Continuing with the embodiment of FIG. 1, the therapy device 113 may additionally include a valve 216 in fluid communication between the pump inlet 212 and the reduced-pressure conduit 158. The valve 216 may have a valve outlet 220, a valve inlet 224, and an ambient air inlet 228. The valve outlet 220 and the valve inlet 224 may be coupled in series between the pump inlet 212 and the reduced-pressure conduit 158 such that fluid communication between the pump inlet 212 and the reduced-pressure conduit 158 is provided through the valve 216. When the valve 216 is open, the valve 216 may permit fluid communication between the reduced-pressure source 192 at the pump inlet 212 and the reduced-pressure conduit 158. When the valve 216 is closed, the valve 216 may preclude fluid communication between the reduced-pressure source 192 at the pump inlet 212 and the reduced-pressure conduit 158. In one embodiment, when the valve 216 is closed, the valve 216 may provide fluid communication between the pump inlet 212 and the ambient air through the ambient air inlet 228.

Continuing with the embodiment of FIG. 1, the controller 200 may be operable to vary a rotational rate of the pump 204 or the time period the pump 204 is on or off. Further, the controller 200 may be operable to simultaneously open and close the valve 216 while varying the rotational rate and/or the time period the pump is on or off. The rotational rate of the pump 204 or the time period the pump is on or off may correspond to the positive pressure output at the pump outlet 208 and the reduced pressure output at the pump inlet 212. However, when the valve 216 is open, the valve 216 may permit reduced pressure from the pump inlet 212 to reach the reduced-pressure conduit 158. When the valve 216 is closed, the valve 216 may preclude reduced pressure from reaching the reduced-pressure conduit 158. Thus, the controller 200 may be operable to control the positive pressure output and the reduced pressure output independently utilizing valve 216. Further, in one embodiment, when the valve 216 is closed, the valve 216 may permit ambient air to reach the pump inlet 212 in order to facilitate the positive pressure output from the pump outlet 208.

The controller 200 may, for example, be electrically coupled in any suitable manner to a solenoid (not shown) operable to open and close the valve 212. In this manner, the controller 200 may vary the voltage output to the solenoid such as, for example, by a binary output, Pulse Width Modulation (PWM), or other output. Further, the controller 200 may be operable to vary the rotational rate of the pump 204 and/or the time the pump 204 is on or off in any suitable manner, such as, for example, by the Pulse Width Modulation (PWM) discussed above. Using Pulse Width Modulation, the rotational rate of the pump 204, the time the pump 204 is on or off, and/or the solenoid may be said to operate based on a duty cycle. An increase in the percentage of the duty cycle may correspond to an increase in the rotational rate of the pump 204 or an increase in the amount of time the pump 204 is on for a given time period. For example, at a 100% duty cycle, the pump 204 may be operating at a maximum output or rotational rate. Similarly, an increase in the percentage of the duty cycle may correspond to an amount of time that the solenoid remains in either an open or a closed state. For example, at a 100% duty cycle, the solenoid may be remain in either an open or a closed state for an entire time period.

In another embodiment, the fluid flow source 184 and the reduced-pressure source 192 may be separate devices individually controlled by the controller 200. For example, the controller 200 may be coupled in any suitable manner to a first solenoid operated valve (not shown) and a second solenoid operated valve (not shown). The first solenoid operated valve may be positioned in fluid communication between the dressing 112 and the fluid flow source 184. The second solenoid operated valve may be positioned in fluid communication between the dressing 112 and the reduced-pressure source 192. The controller 200 may control the flow rate through the first and second valves by, for example, the Pulse Width Modulation (PWM) discussed above.

Continuing with FIGS. 1-5, in operation, the controller 200 may provide reduced pressure from the reduced-pressure source 192 to the reduced-pressure conduit 158 until the manifold pressure signal reaches the target reduced pressure. The controller 200 may monitor the manifold pressure signal and provide reduced pressure accordingly to maintain the reduced pressure in the dressing 112 at the target reduced pressure, or within a threshold thereof. Further, the controller 200 may provide fluid flow from the fluid flow source 184 to the evaporative flow conduit 150, thereby distributing the fluid flow across the exterior surface 134 of the sealing member 118.

As previously described, the manifold 114 and the retention pouch 116 may be formed of permeable materials that act as a manifold for providing fluid communication between the conduit interface 119 and the tissue site 102. Thus, the reduced pressure distributed to the tissue site 102 by the manifold 114 may draw fluid away from the tissue site 102 toward the retention pouch 116 where the fluid may be retained. As depicted by the fluid communication arrows 117 in FIGS. 2-3, the reduced-pressure conduit 158 in the conduit interface 119 may be in fluid communication with the edges 123 of the manifold 114 along the sides of the dressing 112. In this configuration, the dressing 112 may not require fluid communication through the retention pouch 116 in order for reduced pressure applied to the dressing 112 through the reduced-pressure conduit 158 to reach the tissue site 102. Accordingly, when the retention pouch 116 has reached the maximum fluid capacity, the reduced-pressure conduit 158 remains in fluid communication with the tissue site 102 at least by virtue of the fluid communication with the edges 123 of the manifold 114. The fluid communication between the reduced-pressure conduit 158 and the edges 123 may permit the manifold 114 to distribute reduced pressure to the tissue site 102 if, for example, the retention pouch 116 becomes substantially saturated with fluid, or otherwise clogged. In such a configuration, the edges 123 of the manifold 114 may provide an independent fluid communication path between the reduced-pressure conduit 158 and the tissue site 102.

As described above, the retention pouch 116 may include the first and the second permeable layers 126, 127 that encapsulate the absorbent core 128 for retaining fluid during treatment. As shown in FIGS. 2-3, the first permeable layer 126 may be positioned proximate the manifold 114, and the second permeable layer 127 may be positioned proximate the sealing member 118. The fluid acquisition surface 129 of the first permeable layer 126 may face the manifold 114, and the wicking surface 130 of the first permeable layer 126 may face the absorbent core 128. The fluid acquisition surface 129 of the second permeable layer 127 may face the absorbent core 128, and the wicking surface 130 of the second permeable layer 127 may face the sealing member 118.

As fluid contacts the first and the second permeable layers 126, 127, the fluid may be distributed by each of the wicking surfaces 130 along the length of the dressing 112. The grain of each of the wicking surfaces 130 may be oriented along the length of the dressing 112 such that the fluid will follow the direction of the grain by a wicking action without regard to the physical orientation of the dressing 112 at the tissue site 102. As such, the fluid may be distributed and absorbed by the absorbent core 128 in a substantially even manner.

The configuration of the first and the second permeable layers 126, 127 may be particularly useful in managing fluid extracted from the tissue site 102 within the dressing 112. In one embodiment, as fluid contacts the fluid acquisition surface 129 of the first permeable layer 126, the fluid may first be drawn into the retention pouch 116 and away from the manifold 114. Subsequently, the fluid may be wicked along the wicking surface 130 of the first permeable layer 126 for absorption by the absorbent core 128. As fluid contacts the wicking surface 130 of the second permeable layer 127, the fluid may be first wicked along the wicking surface 130 of the second permeable layer 127, away from the sealing member aperture 137. Fluid contacting the second permeable layer 127 may first be wicked away from the sealing member aperture 137 to preclude clogging of the reduced-pressure conduit 158 near the sealing member aperture 137. Clogging can occur, for example, from excess fluid near the sealing member aperture 137. Subsequently, the fluid may be drawn into the retention pouch 116 through the second permeable layer 127 and absorbed by the absorbent core 128. Thus, the configuration and positioning of the first and the second permeable layers 126, 127 relative to one another may direct fluid away from the tissue site 102 and away from the sealing member aperture 137 for storage in the retention pouch 116. In this manner, the tissue site 102 may be kept substantially free of fluids, and the reduced-pressure conduit 158, may be kept substantially free of clogs.

The recess 131 on the retention pouch 116 may further enhance the ability of the dressing 112 to resist clogging. For example, the recess 131 may provide the gap 135 between the inlet 174 of the reduced-pressure conduit 158 and the retention pouch 116 as previously described. The gap 135 may substantially preclude excess fluid from becoming lodged between the sealing member 118 and the retention pouch 116 near the reduced-pressure conduit 158. As an additional precaution, the filter 133 may be positioned in the gap 135 to further preclude excess fluids from reaching the reduced-pressure conduit 158.

Continuing with the operation of the embodiments of FIGS. 1-5, the controller 200 may vary the fluid flow rate from the fluid flow source 184 over the exterior surface 134 of the sealing member 118 according to the amount of fluid retained in the dressing 112. As previously described, one embodiment of the sealing member 118 may comprise a material that has a high MVTR and is thus capable of allowing moisture vapor to egress from the sealed space 132 to the atmosphere through the sealing member 118. Providing fluid flow over the exterior surface 134 of the sealing member 118 may enhance the egress of moisture vapor from the sealed space 132 through the sealing member 118. An increase in the flow rate of the fluid may correspond to an increase in the rate of evaporation of moisture vapor from the sealed space 132.

The controller 200 may vary the fluid flow rate from the fluid flow source 184 based on the previously described differential pressure between the manifold pressure signal and the variable pressure signal. As previously described, the manifold pressure signal may correspond to the pressure measured at the inlet 176 of the manifold pressure conduit 162. Due to the positioning of the inlet 176 between the retention pouch 116 and the manifold 114, the manifold pressure signal may approximate the reduced pressure at the tissue site 102 without regard to the level of fluid saturation in the retention pouch 116. Further, as previously described, the variable pressure signal may corresponds to the pressure measured at the inlet 170 of the variable pressure conduit 154. Due at least in part to the positioning and alignment of the inlet 170 with the expandable portion 121 of the retention pouch 116, the variable pressure signal may vary with increased fluid retention in the retention pouch 116 and the dressing 112. Thus, the differential pressure may correspond to a pressure drop across the retention pouch 116, providing an indication of the level of fluid saturation in the retention pouch 116 and the dressing 112. An increase in the differential pressure may correspond to an increase in the fluid saturation of the retention pouch 116 and the dressing 112. Thus, the controller 200 may increase the flow rate from the fluid flow source 184 in response to an increase in the differential pressure to accelerate the evaporation of the fluid through the sealing member 118.

Initially, the manifold pressure signal, the variable pressure signal, and the reduced pressure applied to the dressing 112 through the reduced-pressure conduit 158 may closely approximate one another. However, as the fluid retained in the retention pouch 116 increases, the variable pressure signal may increase in pressure. For example, the variable pressure signal may become less negative relative to ambient pressure due, at least in part, to the pressure drop created by the fluid in the retention pouch 116. Further, as the fluid in the retention pouch 116 increases, the expandable portion 121 of the retention pouch 116 may increase in size to accommodate the fluid, causing the expandable portion 121 to approach the inlet 170 of the variable pressure conduit 154. When the retention pouch 116 has reached the maximum fluid capacity, the expandable portion 121 of the retention pouch 116 may contact the inlet 170 of the variable pressure conduit 154 and preclude fluid communication between the sealed space 132 and the variable pressure conduit 154. In such a scenario, the controller 200 may provide maximum flow rate from the fluid flow source 184 to remediate the excess fluid. The controller 200 may reduce the flow rate from the fluid flow source 184 as the excess fluid is evaporated and the differential pressure begins to return to a steady state or normal condition, with the variable pressure signal closely approximating the manifold pressure signal.

If the controller 200 cannot remediate the excess fluid within a particular time frame, the controller 200 may provide an alarm indicating, for example, that the dressing 112 needs to be changed. Further, if the manifold pressure signal increases or becomes less negative relative to ambient pressure, the controller 200 may also provide an alarm. Such a variation in the manifold pressure signal may indicate that the manifold 114 has become saturated with fluid and that the tissue site 102 is no longer being provided effective therapy. In one embodiment, the controller 200 may provide an alarm if the manifold pressure signal increases above a threshold amount of the target reduced pressure, such as, for example, a threshold pressure that is about 50% greater than the target reduced pressure. In another embodiment, the controller 200 may provide an alarm after an elapse of a time period input by a user. The alarms provided by the controller 200 may have varying degrees of priority set by a user. For example, a standard alarm may be provided for conditions indicating that the dressing 112 may need to be changed, and a full alarm may be provided for conditions indicating that the tissue site 102 may not be receiving effective treatment. This specification contemplates the use of any suitable devices for providing user inputs and outputs, such as, for example, display panels, key pads, electronic chimes, and other such devices.

Figure 6:
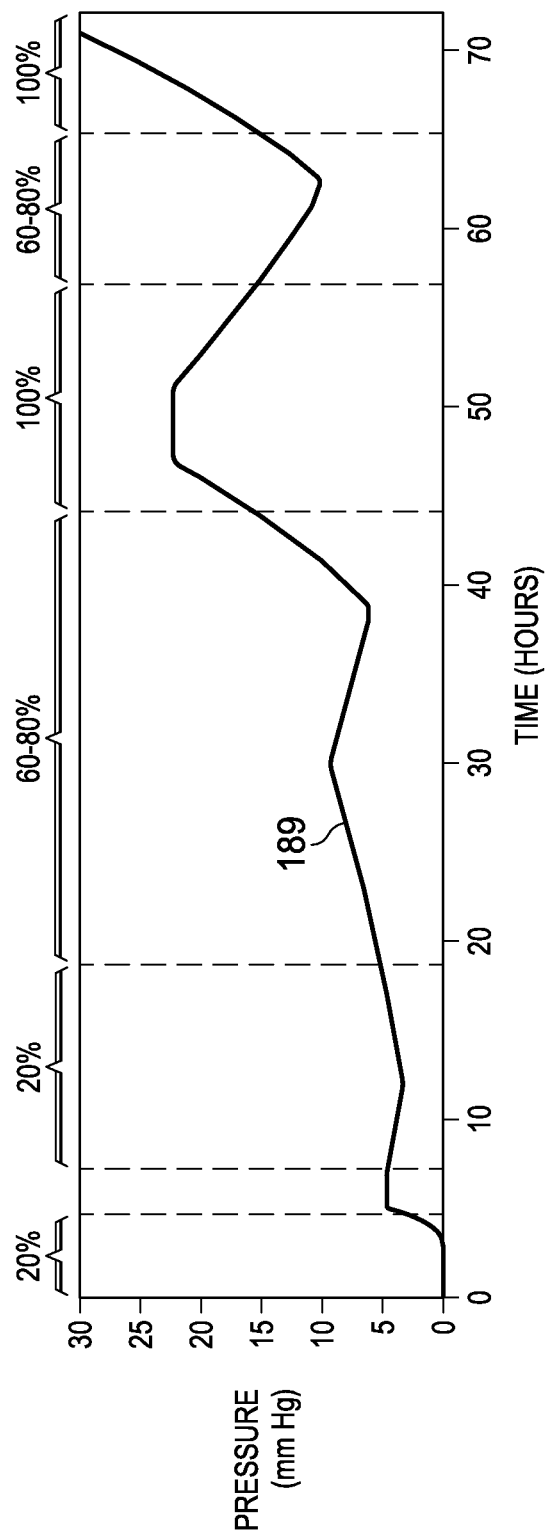
FIG. 6 provides a chart illustrating a plot of differential pressure versus time, and a flow rate corresponding to the differential pressure.

Referring to FIG. 6, a chart is provided that illustrates an exemplary embodiment of the previously described evaporative control features of the treatment system 100. The chart includes the differential pressure (mm Hg) on the vertical axis and time (hours) on the horizontal axis. The plot line 189 on the chart depicts the differential pressure between the manifold pressure signal and the variable pressure signal, or the pressure drop across the retention pouch 116, versus time. When the differential pressure is less than about 5 mm Hg, for example, the controller 200 may provide a 20% duty cycle output for the fluid flow source 184. A differential pressure of less than about 5 mm Hg in this example may require a low evaporation rate, or a low flow rate from the fluid flow source 184, indicating a low or normal level of fluid saturation in the retention pouch 116 and the dressing 112. When the differential pressure is between about 5 mm Hg to about 15 mm Hg, for example, the controller 200 may provide a 60%-80% duty cycle output for the fluid flow source 184. A 60%-80% duty cycle in this example may require a medium evaporation rate, or a medium flow rate from the fluid flow source 184, indicating a medium level of fluid saturation in the retention pouch 116 and the dressing 112. When the differential pressure is greater than about 15 mm Hg, for example, the controller 200 may provide a 100% duty cycle output for the fluid flow source 184. A 100% duty cycle in this example may require a maximum evaporation rate, or a maximum flow rate from the fluid flow source 184, indicating that the retention pouch 116 and the dressing 112 are almost fully saturated with fluid. Thus, as the duty cycle increases in the above examples, the flow rate of fluid from the fluid flow source 184 increases, thereby increasing the evaporation rate of the fluid in the retention pouch 116 and the dressing 112. A differential pressure setting input by a user and corresponding to a desired duty cycle or flow rate may be used to trigger the evaporation rates described above.

The storage, management, and disposition of extracted fluids in the dressing 112 provides many benefits. The potential for clogging as discussed above may be reduced and the storage of fluids within the dressing 112 may eliminate the need for external storage components that could potentially leak or cause discomfort. Further, the reduction in the number of components lowers the volume that must be maintained at reduced pressure, thereby increasing efficiency. Also, the dressing 112 may be capable of managing fluids without regard to any particular physical orientation of the dressing 112 at a tissue site. Additionally, the treatment system 100 employing the dressing 112 may be capable of remediating excess fluids and providing valuable information to a user regarding the status of the therapy and the state of fluid saturation in the dressing 112. Thus, the treatment system 100 and the dressing 112 at least provide increased comfort, usability, efficiency, and confidence that a patient is receiving effective treatment.

This specification additionally provides an illustrative embodiment of a method of treating a tissue site 102 on a patient 101. Referring to the previously described embodiments of FIGS. 1-5, one embodiment of the method may include the step of positioning the first side 120 of the manifold 114 over the tissue site 102. Further, the method may include the steps of positioning the retention pouch 116 over the second side 122 of the manifold 114, and positioning the sealing member 118 to cover the retention pouch 116 and the manifold 114. The method may further include the step of sealingly securing the sealing member 118 to the portion of the epidermis 106 of the patient 101, as described above, to provide the sealed space 132 between the tissue site 102 and the sealing member 118. Additionally, the method may include the step of providing the reduced-pressure conduit 158 in fluid communication with the sealed space 132. As described above, the reduced-pressure conduit 158 may have an inlet 176 positioned in a spaced relationship relative to the recess 131 in the retention pouch 116. The recess 131 may provide a gap 135 between the inlet 176 of the reduced-pressure conduit 158 and the recess 131. The method may include the step of providing a variable pressure conduit 154 in fluid communication with the sealed space 132. As described above, the variable pressure conduit 154 may have an inlet 170 positioned in a spaced relationship relative to the expandable portion 121 of the retention pouch 116. The method may further include the step of measuring a manifold pressure between the manifold 114 and the retention pouch 116. The manifold pressure may correspond to a reduced pressure at the tissue site 102. The method may further include the step of applying reduced pressure to the sealed space 132 through the reduced-pressure conduit 158 until the manifold pressure reaches a target reduced pressure. The reduced pressure may extract fluid from the tissue site 102, and the expandable portion 121 of the retention pouch 116 may expand to retain the fluid. The method may additionally provide the step of measuring a variable pressure between the expandable portion 121 of the retention pouch 116 and the sealing member 118. The method may provide the steps of calculating a differential pressure between the manifold pressure and the variable pressure, and providing a fluid flow over the exterior surface 134 of the sealing member 118. The differential pressure may correspond to the amount of fluid retained by the retention pouch 116. The fluid flow may have a flow rate corresponding to the differential pressure that evaporates the fluid extracted from the tissue site 102.

In one embodiment, the method may include the step of signaling a full alarm if the manifold pressure is greater than a pressure threshold after the manifold pressure initially reaches the target reduced pressure. In another embodiment, the method may include the step of signaling a full alarm after an elapsed time setting input by a user.

In one embodiment, the step of providing a fluid flow over the exterior surface 134 of the sealing member 118 may include the steps of matching the differential pressure with a plurality of differential pressure settings input by a user that correspond to a flow rate, and providing the corresponding fluid flow rate over the exterior surface 134 of the sealing member 118. In another embodiment, at a maximum differential pressure setting, the method includes signaling a full alarm.

In another embodiment, at a maximum differential pressure setting, the method may include the step of comparing an amount of power available to the treatment system 100 with an amount of power required to provide the corresponding fluid flow rate over the sealing member 118 for a time period set by a user. Further, the method may provide the step of signaling an alarm for a supplemental power source if the amount of power available to the treatment system 100 is less that the amount of power required to provide the corresponding fluid flow rate over the sealing member for the time period. Further, the method may provide the steps of canceling the alarm for the supplemental power source if the supplemental power source is provided, and signaling a full alarm if the supplemental power source is not provided. Further, the method may provide the steps of reducing the fluid flow rate over the sealing member 118 according to the differential pressure settings if the differential pressure is less than the maximum differential pressure setting, and signaling a full alarm if the differential pressure is above the maximum differential pressure setting for an elapsed time input by a user.

Figure 7:
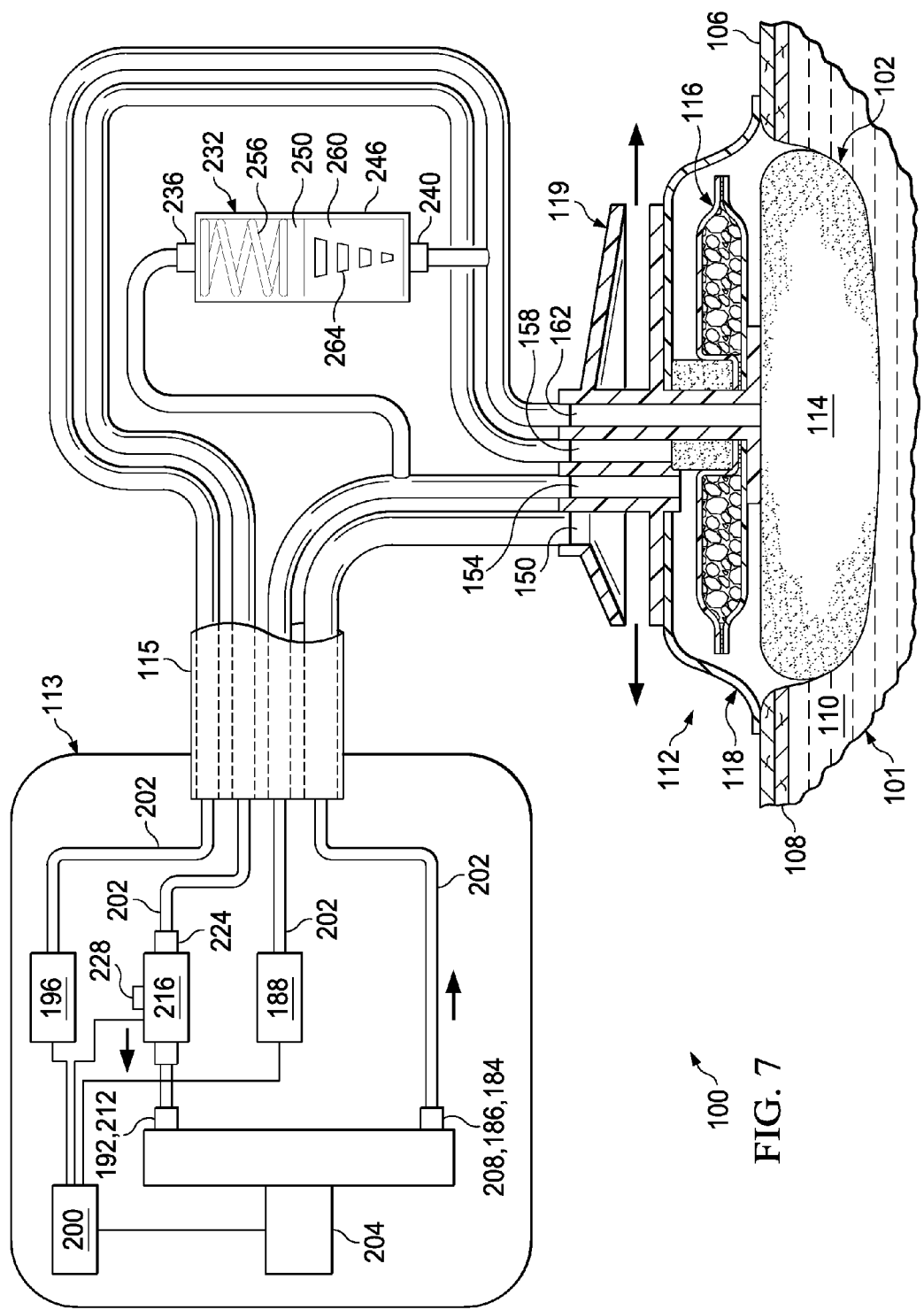
FIG. 7 is a schematic of an another illustrative embodiment of a system for treating a tissue site on a patient.

Referring to an another illustrative embodiment depicted in FIG. 7, the treatment system 100 may include a visual indicator 232 for providing a visual indication of the differential pressure. The visual indicator 232 may include a first port 236 and a second port 240. The first port 236 may be fluidly coupled to the variable pressure conduit 154, and the second port 240 may be fluidly coupled to the manifold pressure conduit 162.

In one embodiment, the visual indicator 232 may include a tube 246 having a piston 250 disposed in the tube 246. The piston 250 may be biased to one end of the tube 246 by a spring 256. The tube 246 may additionally include a transparent window 260 for providing a visual indication of the displacement of the piston 250 in the tube 246. The transparent window 260 may have a plurality of graduated indicators 264 that indicate the differential pressure based upon the displacement of the piston 250 in the tube 246.

In operation, reduced pressure from the variable pressure conduit 154 may be applied to the first port 236, and reduced pressure from the manifold pressure conduit 162 may be applied to the second port 240. The differential pressure between the variable pressure conduit 154 and the manifold pressure conduit 162 may displace the piston 250 in the tube 246. For example, if the reduced pressure at the first port 236 is greater, or more negative relative to ambient pressure, than the reduced pressure at the second port 240, the piston 250 will be displaced in the tube 246 toward the first port 236. If equipped, the graduated indicators 264 may indicate the differential pressure by the displacement of the piston 250 shown through the transparent window 260.

In another embodiment, the visual indicator 232 may include a sensing device such as, for example, a proportional valve, relief valve, or pressure switch (not shown) coupled to the tube 246. The sensing device may detect the displacement of the piston 250 in the tube 246 and generate a signal corresponding to the differential pressure that may be input to the controller 200 and utilized in the evaporative control routine described above.

Although this specification discloses advantages in the context of certain illustrative, non-limiting embodiments, it should be understood that various changes, substitutions, permutations, and alterations can be made without departing from the scope of the specification as defined by the appended claims Further, it will be appreciated that any feature described in connection with any one embodiment may also be applicable to any other embodiment.

What is claimed is:

1. A system for treating a tissue site, comprising:
  a dressing, comprising:
    a manifold adapted to be positioned adjacent the tissue site,
    a retention pouch positioned adjacent the manifold,
    a sealing member having an exterior surface and adapted to cover the retention pouch and the manifold to provide a sealed space between the tissue site and the sealing member, and
    a conduit interface coupled to the sealing member, the conduit interface comprising:
      an evaporative flow conduit in fluid communication with the exterior surface of the sealing member,
      a variable pressure conduit having an inlet in fluid communication with the sealed space, wherein the inlet of the variable pressure conduit is positioned between the retention pouch and the sealing member,
      a reduced-pressure conduit having an inlet in fluid communication with the sealed space, and
      a manifold pressure conduit having an inlet in fluid communication with the manifold and positioned between the retention pouch and the manifold; and
  a therapy device, comprising:
    a fluid flow source in fluid communication with the evaporative flow conduit,
    a variable pressure sensor in fluid communication with the variable pressure conduit,
    a reduced-pressure source in fluid communication with the reduced-pressure conduit,
    a manifold pressure sensor in fluid communication with the manifold pressure conduit, and
    a controller adapted to receive a variable pressure signal from the variable pressure sensor and a manifold pressure signal from the manifold pressure sensor, wherein the controller is operable to provide a reduced pressure output from the reduced-pressure source when the manifold pressure signal is greater than a target reduced pressure, and wherein the controller is operable to increase a fluid flow rate from the fluid flow source in response to an increase in a pressure differential between the variable pressure signal and the manifold pressure signal.

2. The system of claim 1, wherein the manifold comprises a hydrophobic material that is fluid permeable.

3. The system of claim 1, the retention pouch adapted to retain a fluid and comprising an expandable portion and a recess, wherein the expandable portion expands to retain the fluid and the recess is substantially precluded from expansion, and wherein the recess is formed by coupling a first permeable layer to a second permeable layer.

4. The system of claim 3, wherein the inlet of the variable pressure conduit is positioned in a spaced relationship relative to the expandable portion of the retention pouch, and wherein the inlet of the reduced-pressure conduit is positioned in a spaced relationship relative to the recess in the retention pouch.

5. The system of claim 1, wherein a portion of the sealing member is comprised of a material that allows vapor to egress from the sealed space through the sealing member.

6. The system of claim 3, further comprising a filter positioned in a gap provided by the recess, wherein the gap is positioned between the inlet of the reduced-pressure conduit and the recess in the retention pouch.

7. The system of claim 1, wherein the inlet of the reduced-pressure conduit is positioned between the retention pouch and the sealing member.

8. The system of claim 1, wherein the inlet of the manifold pressure conduit is positioned adjacent to the manifold.

9. The system of claim 1, wherein the manifold and the retention pouch provide fluid communication between the reduced-pressure conduit and the tissue site, and wherein when the retention pouch has reached a maximum fluid capacity, the reduced-pressure conduit is in fluid communication with the tissue site at least through an edge of the manifold.

10. The system of claim 3, wherein when the retention pouch has reached a maximum fluid capacity, the expandable portion of the retention pouch contacts the inlet of the variable pressure conduit and substantially precludes fluid communication between the sealed space and the variable pressure conduit.

11. The system of claim 1, wherein the conduit interface further comprises an evaporative flow outlet in fluid communication with the evaporative flow conduit, wherein the evaporative flow outlet is positioned circumferentially about the conduit interface.

12. The system of claim 3, wherein the conduit interface further comprises a base coupled at the inlet of the manifold pressure conduit and extending laterally therefrom, wherein the retention pouch is carried between the base and the sealing member, and wherein the expandable portion of the retention pouch extends laterally beyond the base.

13. The system of claim 1, wherein the reduced-pressure source and the fluid flow source are a pump, the pump having a pump inlet and a pump outlet, wherein the pump inlet is in fluid communication with the reduced-pressure conduit and the pump outlet is in fluid communication with the evaporative flow conduit.

14. The system of claim 13, wherein the therapy device further comprises a valve in fluid communication between the pump inlet and the reduced-pressure conduit, wherein the controller is operable to open and close the valve, wherein when the valve is open, the pump inlet is in fluid communication with the reduced-pressure conduit, and wherein when the valve is closed, the valve substantially precludes fluid communication between the pump inlet and the reduced-pressure conduit.

15. The system of claim 14, wherein when the valve is closed, the pump inlet is in fluid communication with ambient air.

* * * * *